(12) United States Patent
Frazier

(10) Patent No.: US 8,856,988 B2
(45) Date of Patent: Oct. 14, 2014

(54) ADJUSTABLE SUPPORT FOR A RESIDUAL LIMB OF AN AMPUTEE

(76) Inventor: Michael O. Frazier, La Vernia, TX (US)

( * ) Notice: Subject to any disclaimer, the term of this patent is extended or adjusted under 35 U.S.C. 154(b) by 335 days.

(21) Appl. No.: 13/270,007

(22) Filed: Oct. 10, 2011

(65) Prior Publication Data

US 2012/0084925 A1   Apr. 12, 2012

Related U.S. Application Data

(60) Provisional application No. 61/392,368, filed on Oct. 12, 2010.

(51) Int. Cl.
*A47C 17/86* (2006.01)
*A61F 2/60* (2006.01)
*A61F 2/50* (2006.01)
*A61F 2/78* (2006.01)

(52) U.S. Cl.
CPC ........... *A61F 2/601* (2013.01); *A61F 2002/502* (2013.01); *A61F 2002/5084* (2013.01); *A61F 2002/7862* (2013.01); *A61F 2002/7881* (2013.01)
USPC ........................................ 5/624; 5/648; 5/661

(58) Field of Classification Search
USPC .............................. 5/621–624, 646–651, 661
See application file for complete search history.

(56) References Cited

U.S. PATENT DOCUMENTS

| | | | | |
|---|---|---|---|---|
| 4,913,393 A * | 4/1990 | Wood | ......................... | 248/230.2 |
| 5,121,743 A * | 6/1992 | Bishop | ............................ | 602/22 |
| 5,291,903 A * | 3/1994 | Reeves | ........................... | 128/878 |
| 5,353,809 A * | 10/1994 | Faucher | ............................ | 5/646 |
| 5,464,443 A | 11/1995 | Wilson et al. | | |
| 6,629,944 B2 * | 10/2003 | Smart | ............................ | 602/36 |
| 7,337,483 B2 * | 3/2008 | Boucher et al. | ................... | 5/621 |
| 7,669,934 B1 * | 3/2010 | Cline | ....................... | 297/423.45 |
| 7,832,035 B2 * | 11/2010 | Walczyk | ........................... | 5/648 |
| 7,934,687 B2 * | 5/2011 | Crook et al. | .................. | 248/168 |
| 2005/0160533 A1 * | 7/2005 | Boucher et al. | ................... | 5/647 |
| 2008/0172791 A1 * | 7/2008 | Walczyk | ........................... | 5/623 |
| 2010/0263129 A1 * | 10/2010 | Aboujaoude | .................... | 5/650 |
| 2011/0143898 A1 * | 6/2011 | Trees | ........................... | 482/142 |

* cited by examiner

*Primary Examiner* — William Kelleher
(74) *Attorney, Agent, or Firm* — Gunn, Lee & Cave, P.C.

(57) ABSTRACT

A support structure for an amputee that has lost his foot is shown. The support structure is adjustable vertically and may be removably attached to the residual limb to support the residual limb when the amputee is in a wheelchair or is sitting upright in a seat or chair. The vertical height is adjusted by a spring-loaded pin and telescopic members. Pads provide cushions for the residual limb.

2 Claims, 10 Drawing Sheets

ADJUSTABLE SUPPORT FOR A RESIDUAL LIMB OF AN AMPUTEE

BACKGROUND OF THE INVENTION

1. Field of the Invention

The present invention relates to support for a residual limb of an amputee and, more particularly, to an adjustable leg support for the residual limb of a leg member of an amputee.

2. Background of the Invention.

The last several decades has resulted in a tremendous increase in knowledge on how to treat amputees. Many advances have been made in prosthetic devices to accommodate amputees. The prosthetic devices are adjustable in many different ways to accommodate people of all different sizes and structure.

Applicant himself is an amputee that had his right leg and foot removed below the knee due to diabetes. During the period of recovery, Applicant was in a wheelchair until he was fitted with a foot prosthesis. While riding in the wheelchair or sitting upright in a chair, the residual limb would hang down because there was no foot on the end of the residual limb to provide support. This causes the hamstrings, quadriceps and muscles in the hip to undergo atrophy and flexion contracture due to the limited use of these muscles.

Flexion contracture is the shrinking and stiffening of the muscle as the muscle fibers contract across each other due to the non-use or limited use of these muscles. Contracture of the quadriceps, hamstrings and hip muscles is very painful to the amputee. Providing support for the residual limbs helps to fight against the flexion contractures to reduce or prevent the shrinking of the muscles, and thus alleviating or reducing the pain to the amputee.

Various exercises are often recommended by doctors or physical therapists to amputees to fight against flexion contracture. It may be advisable to perform various knee extension and flexion exercises as well as hip, quadriceps and hamstring extension and flexion exercises. Such exercises stretch the contracting muscles to combat the shrinking and stiffening. Another way amputees have combated flexion contractures is to lie prone on their front side. However, many amputees do not like to lie in the prone position to combat the flexion contractures. Moreover, it is not always possible to perform the exercises necessary to combat flexion contractures.

Applicant noticed during his rehabilitation after surgery when his foot was removed, if he provided support for the residual limb so that it did not dangle when he was in a seated position, his muscles did not get contractures which caused the muscles of his residual limb to hurt. As a result, Applicant designed a structure that was adjustable in height to support his residual limb to avoid flexion contractures. The present invention is directed toward such a support structure.

BRIEF SUMMARY OF THE INVENTION

It is an object of the present invention to provide support for a residual limb, especially a residual leg.

It is another object of the present invention to provide an adjustable support for a residual limb that has been amputated below the knee.

It is yet another object of the present invention to provide a support for a residual limb, which support has an adjustable structure, a supporting plate and padding for the residual limb.

It is yet another object of the present invention to provide a support structure for a residual limb that can be quickly attached to or disconnected from the residual limb.

A curved plate is attached to the top of a telescopic member that has a downwardly extending leg. The leg may be extended or retracted by a spring-loaded pin contained therein. The plate has foam on the top thereof, which foam has a soft, felt-covered top foam and a harder lower foam bonded thereto, both of which provide elastic support for the residual limb.

Elastic straps extend up through slots in the sides of the plate and around the residual limb, which straps have Velcro® on the ends thereof. By use of the straps, the straps can be wrapped around the residual limb so the entire supporting device can be held in place. The leg on the supporting device can be extended or retracted as necessary to adjust the height. Therefore, the amputee can be sitting in a wheelchair, a regular chair or some other type of sitting structure, where one foot supports the good leg and the support structure supports the residual limb.

DESCRIPTION OF THE PREFERRED EMBODIMENT

Figure 1:
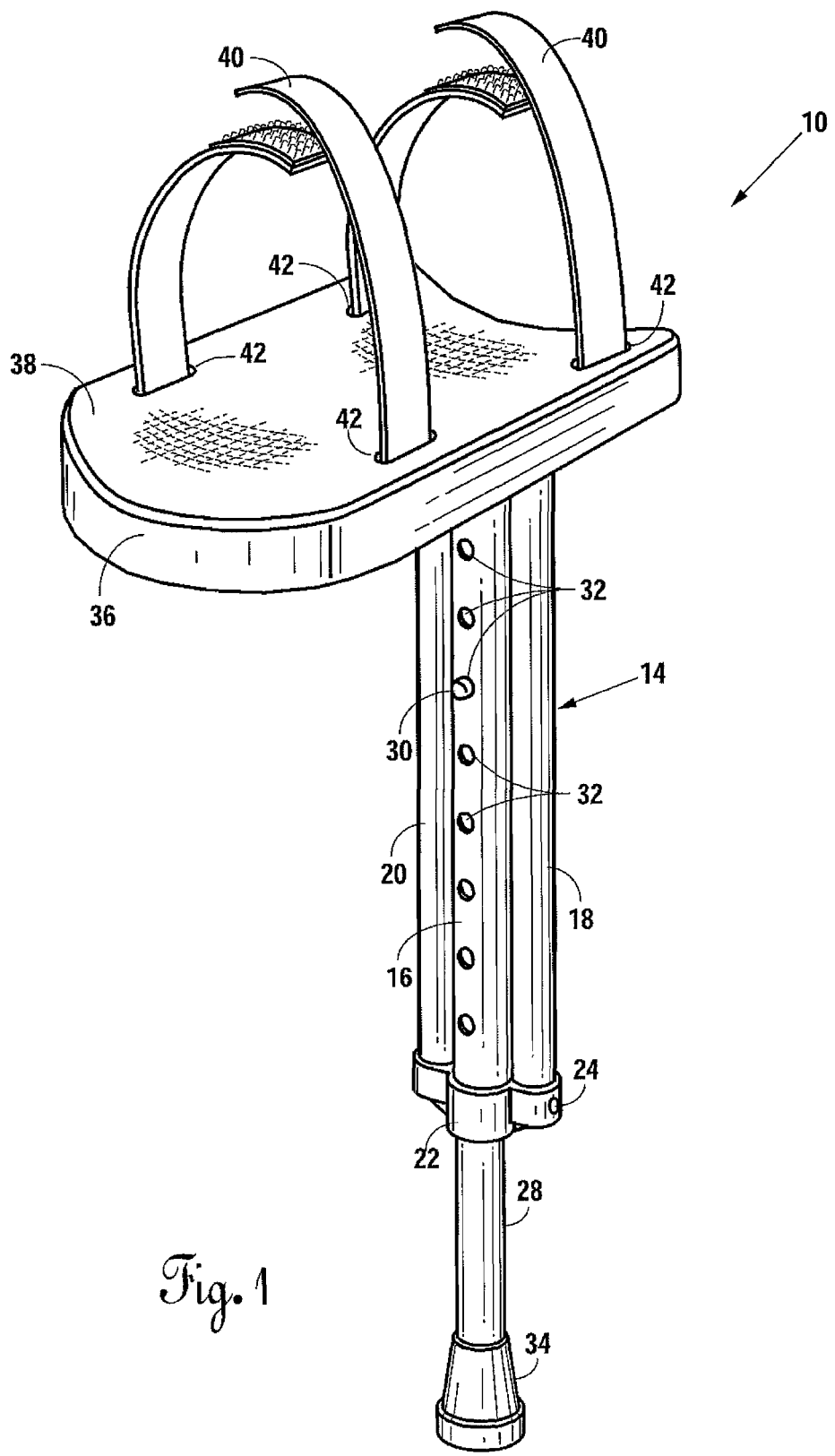
FIG. 1 is a perspective view of a support structure for a residual limb after a foot has been amputated.
Figure 2:
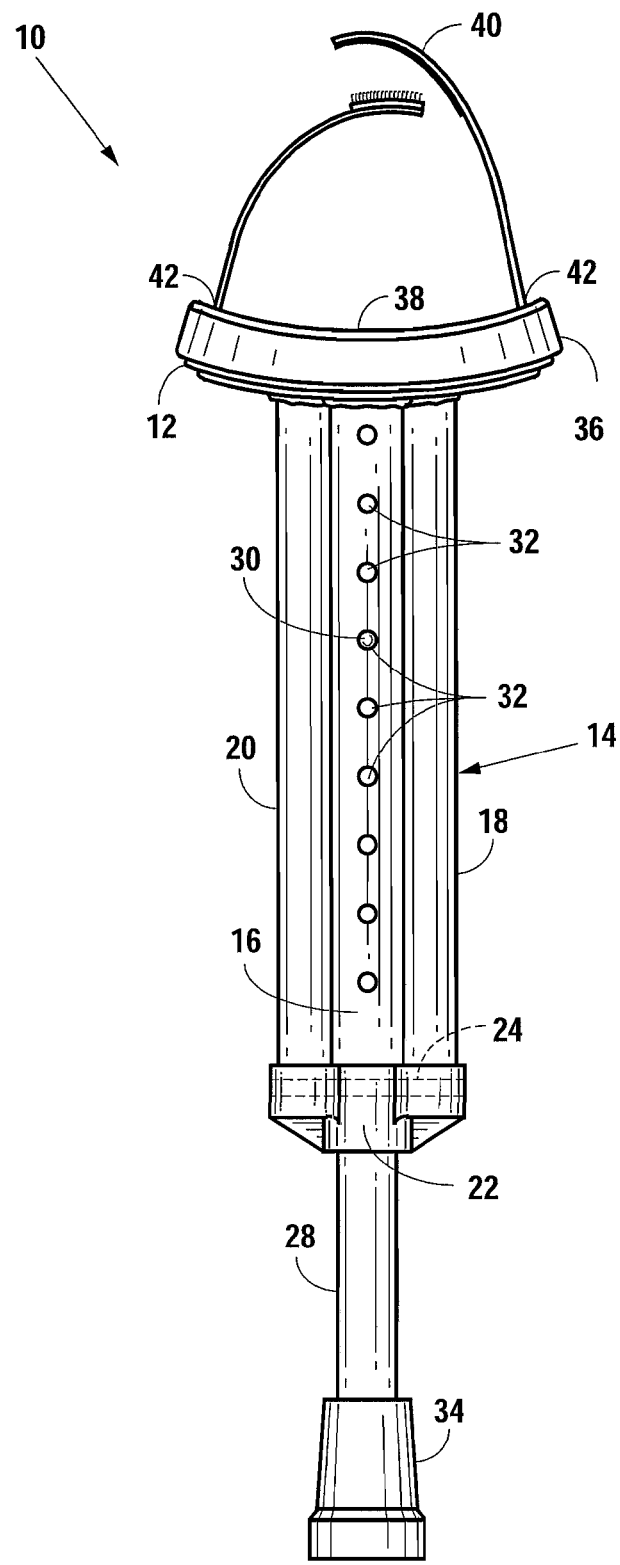
FIG. 2 is a front elevated view of FIG. 1.
Figure 3:
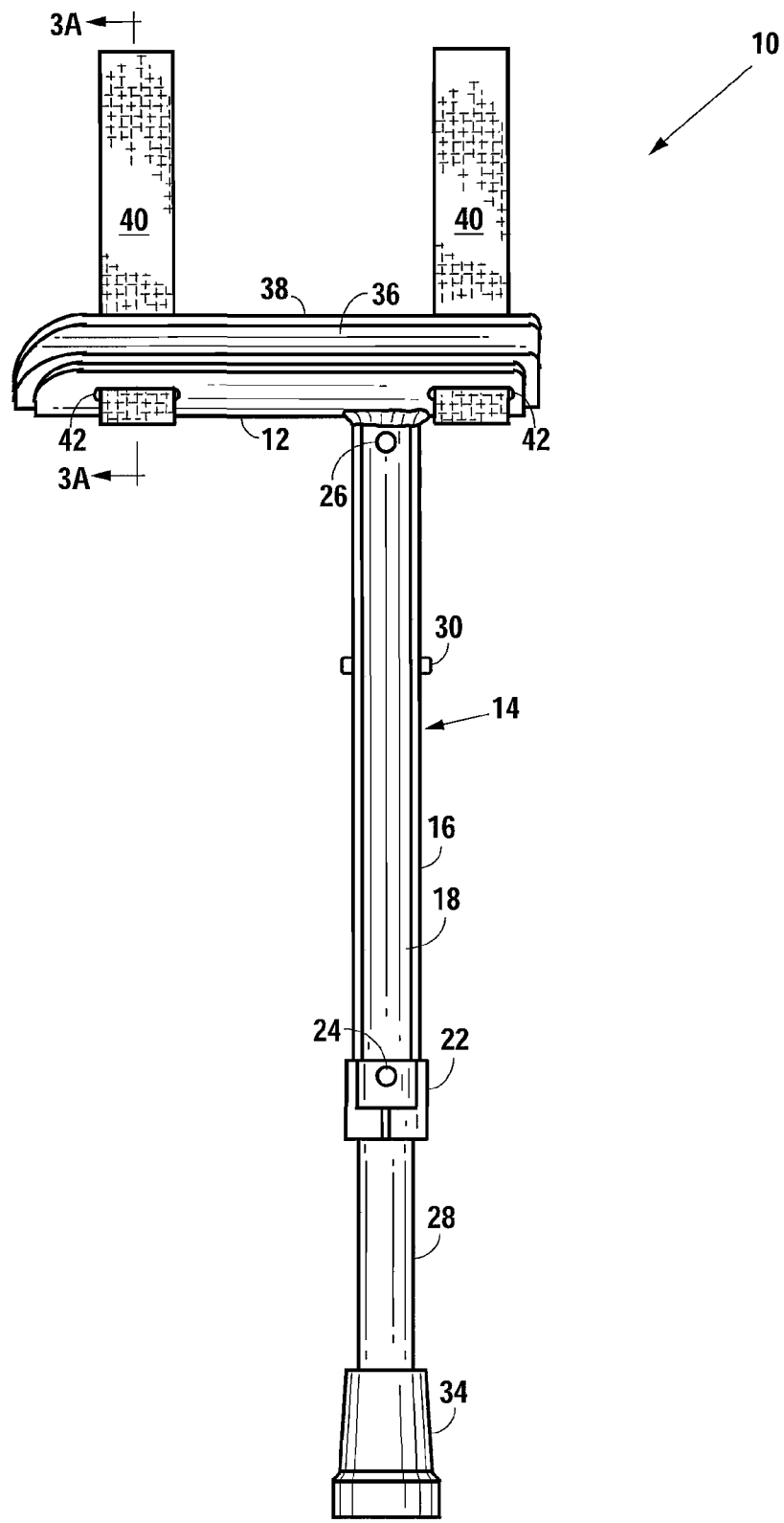
FIG. 3 is a side elevated view of FIG. 1
Figure 3A:
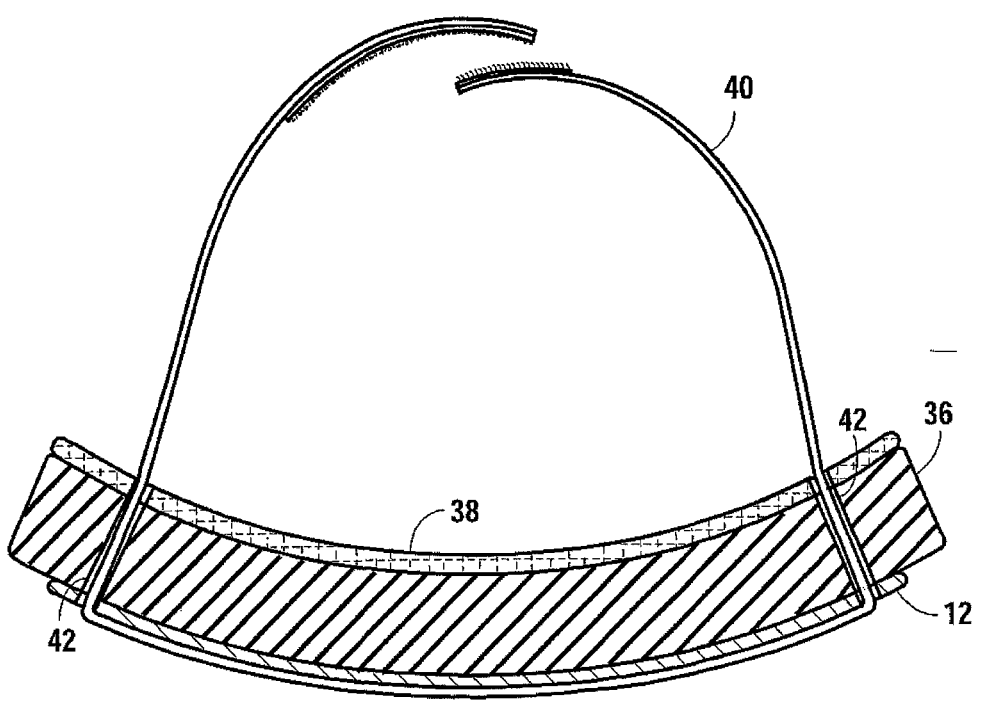
FIG. 3A is a cross-sectional view of FIG. 3 along section lines 3A-3A.

Referring to FIGS. 1, 2, 3 and 3A in combination, a support structure 10 for someone that has had a foot amputated is shown. A support structure 10 has a plate 12 made from suitable material such as aluminum, which plate 12 is slightly curved as shown in FIGS. 3 and 3A. The curvature of plate 12 is of approximately the appropriate curvature to comfortably receive the posterior portion of the residual limb 46 (see FIG. 4) of the person. The plate 12 may be made from a non-corrosive material such as aluminum and has sufficient thickness to support someone putting their leg weight thereon. However, plate 12 may also be made of any other material suitable to support the weight of a person's leg thereon.

Attached to the plate 12 by welding or any other suitable attaching device or attaching method is a downwardly extending telescopic member 14. To give sufficient rigidity to the downwardly extending telescopic member 14, it has an enlarged central tubular member 16 reinforced by side tubular members 18 and 20. All three of the tubular members 16, 18, and 20 are attached to the plate 12 by any suitable device such as a screw or other attaching device, or by any suitable attaching method such as welding. The lower ends of the side tubular members 18 and 20 are connected to the enlarged central tubular member 16 by a specially designed tubular bracket 22. The tubular bracket 22 has a pin 24 extending into tubular members 18 and 20, but not enlarged central tubular member 16. Also as additional support, an upper pin 26 (see FIG. 3) goes through the top of the tubular members 16, 18 and 20.

Extending downward from the enlarged central tubular member 16 is a tubular leg 28 that is designed to snuggly fit therein. The tubular leg 28 has a spring-loaded pin 30 that extends out of the front and the back of the enlarged central tubular member 16 through adjustment holes 32 located therein. By pressing the spring-loaded pin 30, the tubular leg 28 can be adjusted up or down. On the lower end of the tubular leg 28 is located a rubber foot 34. The rubber foot 34 may be similar to the rubber foot located on the lower end of many hand crutches.

Referring now to the plate 12, located there above is a fairly firm foam pad 36 that is flexible, yet is fairly firm. Because the weight of the residual limb 46 is supported by the foam pad 36, it is important that foam pad 36 have some elasticity without being either too firm or too soft.

Attached to the top of the fairly firm foam pad 36 is a felt-covered, soft foam layer 38. See FIG. 3A. The felt-covered soft foam layer 38 contacts the residual limb 46 when the support structure 10 is being used. The felt-covered soft foam layer 38 is normally bonded to the fairly firm foam pad 36.

It is important that the fairly firm foam pad 36 remain on top of the plate 12. It is also important that when the residual limb is moved, the support structure 10 move with the residual limb 46. Therefore, elastic straps 40 with Velcro® thereon are provided that extend upward through slots 42 in the plate 12, fairly foam pad 36 and the felt-covered soft foam layer 38. The slots 42 provided in the plate 12, fairly foam pad 36 and felt-covered foam layer 38, all match up to receive the elastic straps there through.

In one embodiment, the fairly firm foam pad 36 is bonded to the plate 12 using any suitable adhesive (not shown). However, with the elastic straps 40 running through the slots 42, bonding is not absolutely necessary. Therefore, in another embodiment, the fairly firm foam pad 36 is not bonded to plate 12

Figure 4:
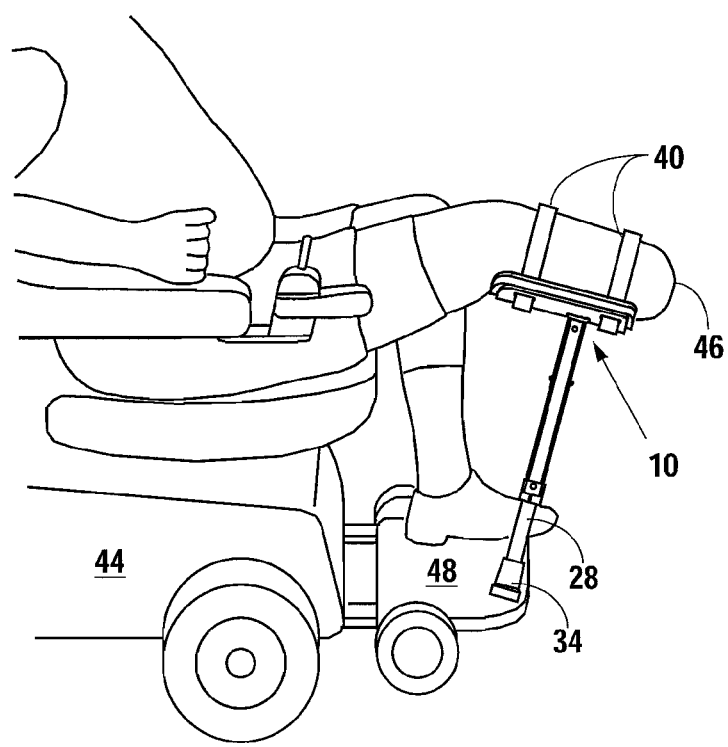
FIG. 4 is a perspective view of an amputee using the present invention in a wheelchair to support a residual limb after amputation of a foot.

Referring to the environmental view shown in FIG. 4, an individual that has lost a foot is riding in a motorized wheelchair 44. Supporting the residual limb 46 of the individual is the support structure 10. The elastic straps 40 hold the support structure 10 to the residual limb 46. The rubber foot 34 rests on the foot rest 48 of the motorized wheelchair 44. The height of the support structure 10 can be adjusted by adjusting the tubular leg 28. In this manner the residual limb 46 is supported to the same height as the other leg of the individual. If it is desired to stretch the hamstrings, the height of the support structure 10 can be raised by adjusting tubular leg 28. Moreover, if the amputation occurred below the knee of the person, and it is desired to stretch the quadriceps, lowering the support structure 10 by adjusting the tubular leg 28 allows the person to partially retract the lower portion of the residual limb 46 toward the hamstrings to stretch the quadriceps. In this manner, extension is exerted on the hamstrings or quadriceps. This keeps flexion contractures from occurring in the amputee.

Figure 5:
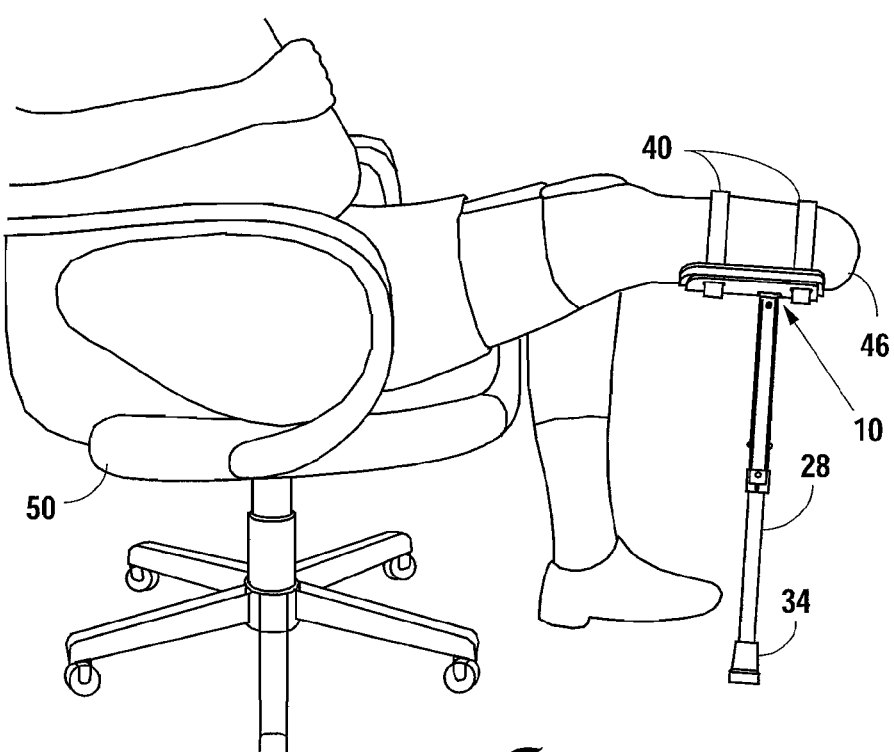
FIG. 5 is a perspective view of an amputee using the present invention in a chair to support a residual limb after amputation of a foot.

If the amputee is setting in a chair 50, as illustrated in FIG. 5, again the support structure 10 supports the residual limb 46. Again, the elastic straps 40 hold the support structure 10 to the residual limb 46. Also, the height of the support structure 10 can be adjusted by adjusting tubular leg 28 so that when the rubber foot 34 rests on the floor, the residual limb 46 will be maintained at approximately the same elevation as the other leg of the person. Again, operation of the tubular leg 28 to raise or lower the support structure 10 allows for extension or stretching of the muscles as previously described, which will prevent flexion contractures or flexion contractures in the amputee.

Figure 6:
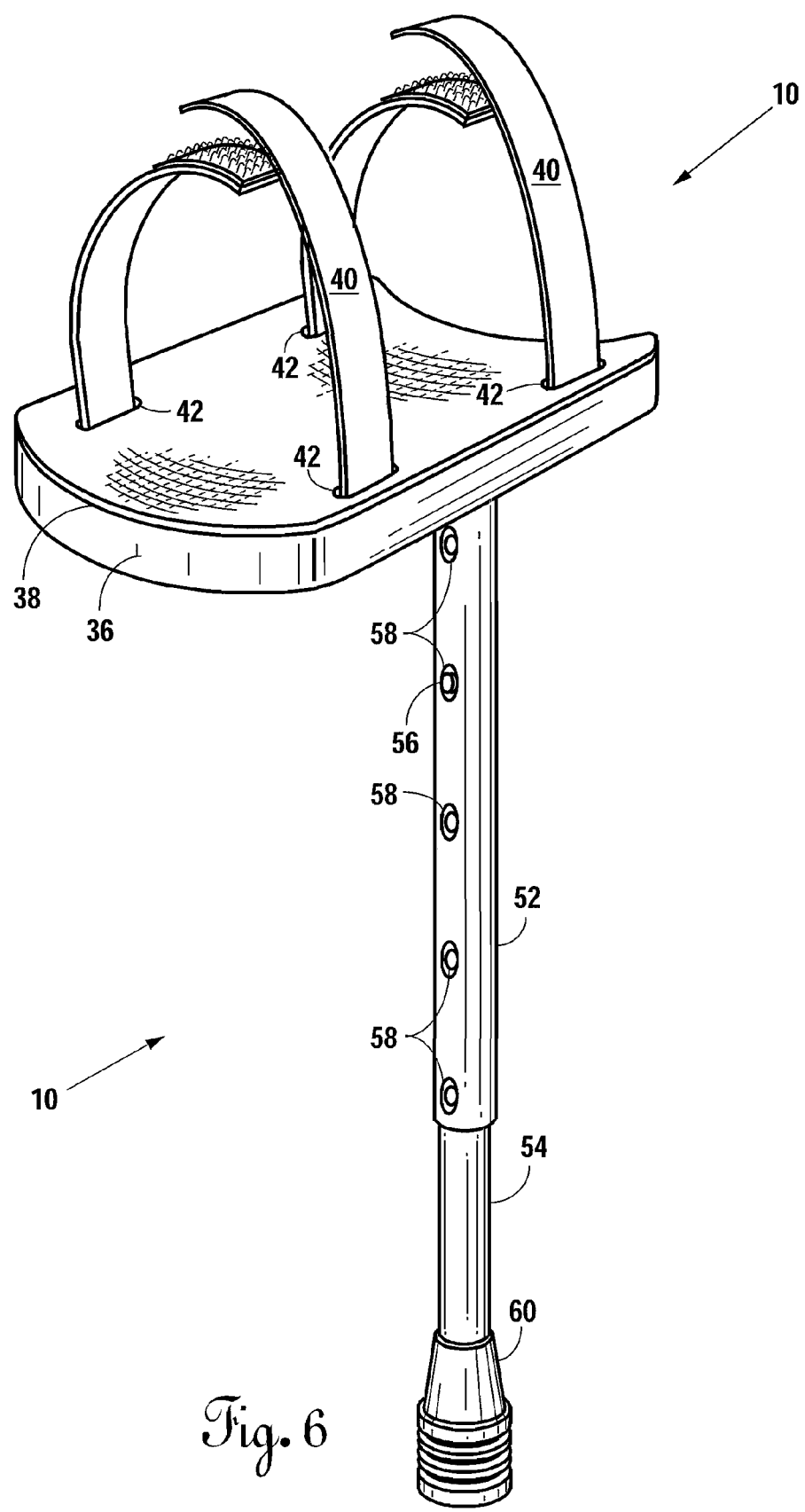
FIG. 6 is a perspective view of an embodiment of the support structure of the present invention.
Figure 7:
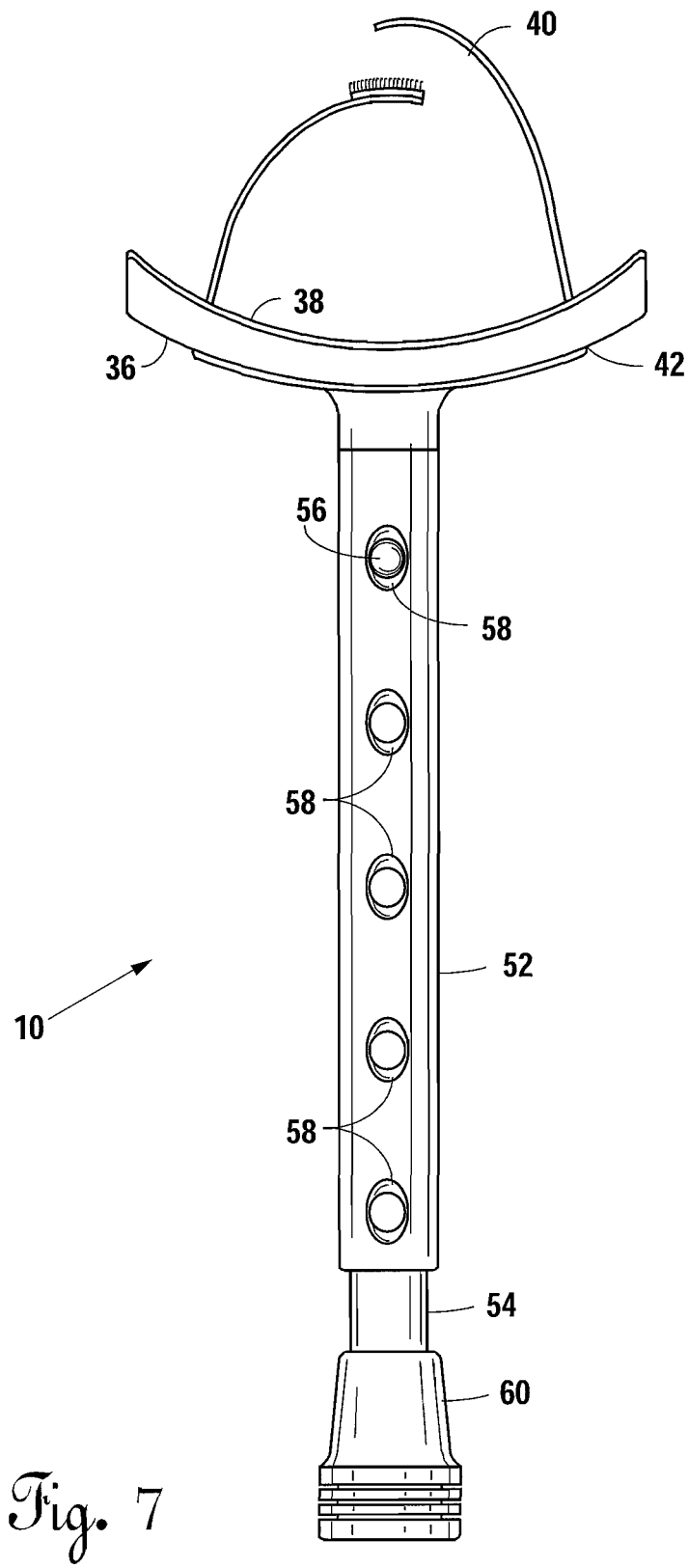
FIG. 7 is a front view of FIG. 6.
Figure 8:
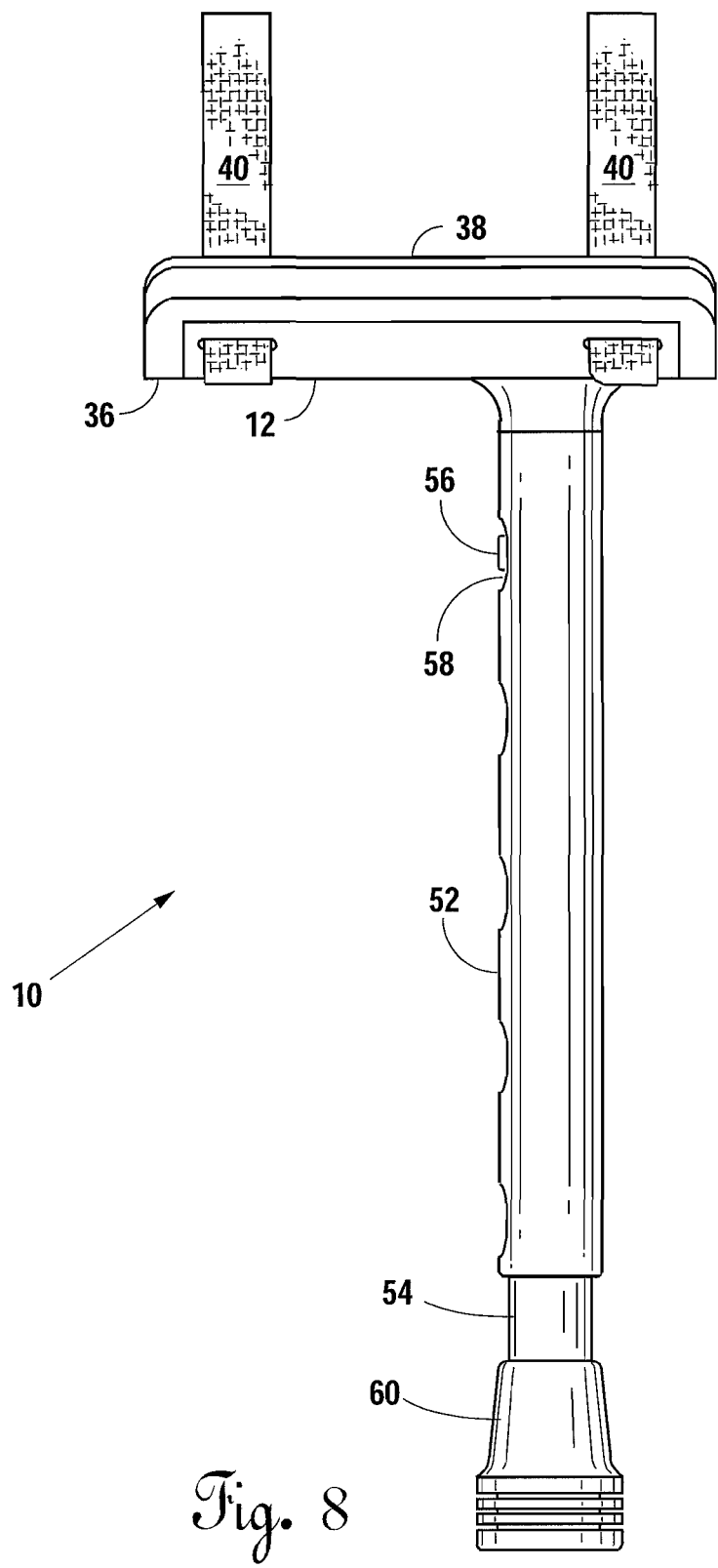
FIG. 8 is a side view of FIG. 6.
Figure 9:
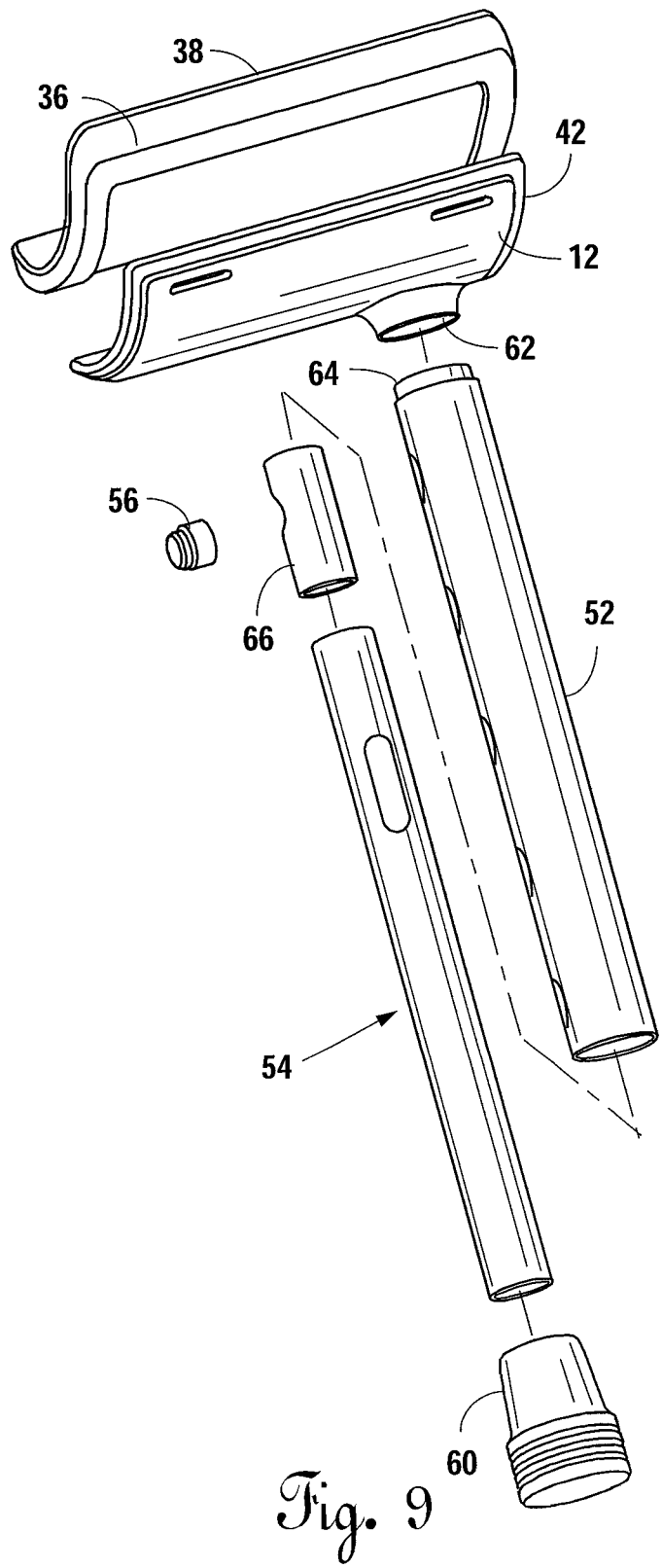
FIG. 9 is an exploded view of the support structure of the present invention.
Figure 10:
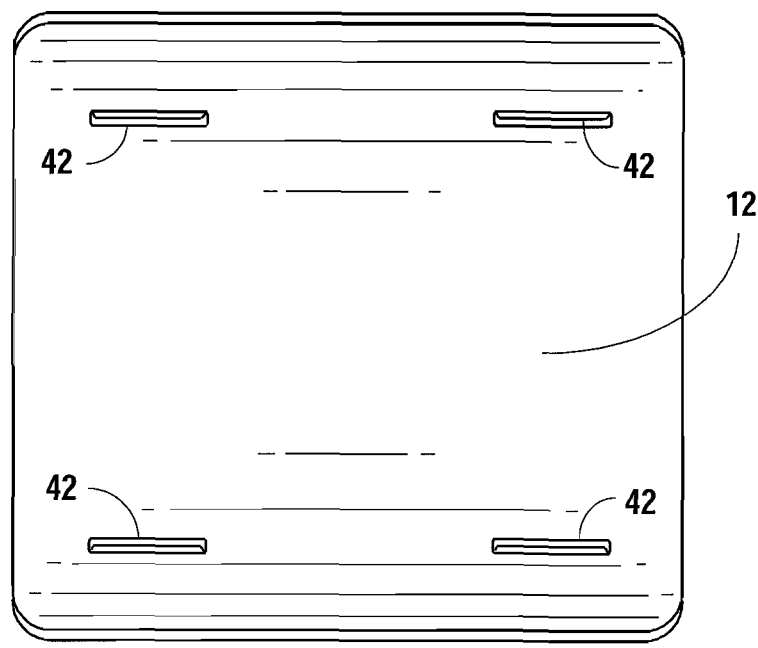
FIG. 10 is a bottom view of the plate of the support pad of the present invention.

Referring now to FIGS. 6, 7, 8, 9 and 10, the preferred embodiment of the support structure 10 is shown. In the preferred embodiment as shown in FIG. 6, downwardly extending telescoping member 14 has been replaced with a single tubular member 52 that is attached to the plate 12. As shown in FIG. 9, plate 12 has a predefined slot 62 for receiving top end 64 of single tubular member 52 therein. Top end 64 is slightly smaller in diameter than the rest of tubular member 52, defining a shoulder for resting along the periphery of predefined slot 62 of plate 12. Once top end 64 is inserted within slot 62, tubular member 52 is secured to plate 12 by any suitable method such as welding, or any suitable attaching device such as screws (not shown) or other suitable attaching device. Telescopically received in the lower end of a single tubular member 52 is tubular leg 54. Tubular leg 54 has spring-loaded pins 56 therein. Spring loaded pin 56 is disposed within pin housing 66, and is biased through the hole in pin housing by a spring (not shown). Pin housing is telescopically disposed within tubular leg 54. Spring loaded pin 56 is biased outward, through the hole in tubular leg 54 to keep pin housing 66 from sliding within tubular leg 54. Spring-loaded pin 56 can adjust the height of the tubular leg 54 by adjustment holes 58 in the same manner previously described. The lower end of the tubular leg 54 has a rubber foot 60 thereon. Adjusting the height of the support structure 10 by adjusting the height of the tubular leg 54 allows for the extension and stretching of the residual limb 46 muscles in the same manner described with regard to the embodiment shown in FIGS. 1-4.

The fairly firm foam pad 36, felt-covered soft foam layer 38, elastic straps 40 and slots 42 are assembled on plate 12 in the same manner as shown and described in embodiment shown in FIGS. 1-4 and hence bear the same numbers.

Although the invention has been described with reference to specific embodiments, this description is not meant to be construed in a limited sense. Various modifications of the disclosed embodiments, as well as alternative embodiments of the invention will become apparent to persons skilled in the art upon the reference to the description of the invention. It is therefore contemplated that the appended claims will cover such modifications that fall within the scope of the invention.

I claim:

1. A method for combating contracture of muscles in the residual limb of an amputee comprising the steps of:

sitting substantially upright;

placing a posterior portion of said residual limb on a padding structure of a portable supporting device, said portable supporting device comprising a concave plate adjacently below said padding structure, a tubular member adjacently below said concave plate and extending downward therefrom, a tubular leg telescopically disposed within said tubular member, and a height adjustment device to adjust the height of said portable supporting device;

attaching said portable supporting device to said residual limb after said placing step;

adjusting said height of said supporting device to stretch said muscles in said residual limb of said amputee;

said portable supporting device comprises a plurality of slots along a periphery of said plate, and extending through said padding structure, and at least one strap extending through said slots, and said attaching step comprises strapping said portable supporting device to said residual limb.

2. The method as recited in claim 1 wherein said adjusting step comprises the steps of:

compressing a spring-loaded pin, said spring loaded pin being disposed within said tubular leg, extending through a hole there through, and extending through at least one of a plurality of vertical holes on said tubular member;

sliding said tubular leg within said tubular member to adjust said height of said supporting device;

aligning said spring-loaded pin with said at least one of said plurality of vertical holes of said tubular member; and releasing said spring-loaded pin.

* * * * *